US012213719B2

(12) United States Patent
Yang et al.

(10) Patent No.: US 12,213,719 B2
(45) Date of Patent: Feb. 4, 2025

(54) CRYOADHESION APPARATUS

(71) Applicant: ACCU TARGET MEDIPHARMA (SHANGHAI) CO., LTD., Shanghai (CN)

(72) Inventors: Chi Yang, Shanghai (CN); Zhaohua Chang, Shanghai (CN)

(73) Assignee: ACCU TARGET MEDIPHARMA (SHANGHAI) CO., LTD., Shanghai (CN)

( * ) Notice: Subject to any disclaimer, the term of this patent is extended or adjusted under 35 U.S.C. 154(b) by 307 days.

(21) Appl. No.: 17/626,241

(22) PCT Filed: Sep. 29, 2020

(86) PCT No.: PCT/CN2020/118706
§ 371 (c)(1),
(2) Date: Jan. 11, 2022

(87) PCT Pub. No.: WO2021/189800
PCT Pub. Date: Sep. 30, 2021

(65) Prior Publication Data
US 2023/0000537 A1    Jan. 5, 2023

(30) Foreign Application Priority Data

Mar. 23, 2020   (CN) .......................... 202010205281.X

(51) Int. Cl.
*A61B 18/02*   (2006.01)
*A61B 18/00*   (2006.01)

(52) U.S. Cl.
CPC ..... *A61B 18/0218* (2013.01); *A61B 2018/00017* (2013.01); *A61B 2018/0094* (2013.01);

(Continued)

(58) Field of Classification Search
CPC ..... A61B 18/02; A61B 18/1815; A61B 18/14; A61B 18/1477; A61B 18/0218;
(Continued)

(56) References Cited

U.S. PATENT DOCUMENTS

| 6,039,730 A * | 3/2000 | Rabin .................. A61B 90/17 606/22 |
| 2015/0148791 A1 * | 5/2015 | Birdsall .................. A61B 18/02 606/22 |

(Continued)

FOREIGN PATENT DOCUMENTS

| CN | 107174297 A | 9/2017 |
| CN | 107530116 A | 1/2018 |

(Continued)

*Primary Examiner* — Khadijeh A Vahdat
*Assistant Examiner* — Marina Delaney Templeton
(74) *Attorney, Agent, or Firm* — NZ Carr Law Office PLLC

(57) ABSTRACT

A cryoadhesion apparatus includes a remote control assembly, a valve assembly, a needle catheter assembly, and a gas cylinder, the remote control assembly includes a sheath structure and a remote control, the sheath structure is provided with a catheter channel for the needle catheter assembly to pass through, two ends of the valve assembly are respectively connected to the needle catheter assembly and the gas bottle; the sheath structure is capable of squeezing the needle catheter assembly, when squeezing is maintained, the needle catheter assembly is capable of moving along with the sheath structure under a frictional force between an inner wall of the catheter channel and the needle catheter assembly; the remote control is configured to, when triggered, send a trigger signal to the valve assembly; the valve assembly is configured to transport, when receiving the trigger signal, a gas from the gas cylinder to the needle catheter assembly.

20 Claims, 8 Drawing Sheets

(52) U.S. Cl.
CPC ............... *A61B 2018/0262* (2013.01); *A61B 2018/0293* (2013.01)

(58) Field of Classification Search
CPC ........... A61B 2018/00577; A61B 2018/00005; A61B 2018/00023; A61B 2018/00791; A61B 2018/0212; A61B 2018/00642; A61B 2018/0702; A61B 2018/00982; A61B 2018/00708; A61B 2018/0262; A61B 2018/00922; A61B 2018/0293; A61B 2018/0231; A61B 2018/00017; A61B 2018/0094; A61B 2018/00744; A61B 2018/0091; A61B 2018/1475
See application file for complete search history.

(56) References Cited

U.S. PATENT DOCUMENTS

| | | | |
|---|---|---|---|
| 2017/0042571 A1* | 2/2017 | Levi | A61M 25/0113 |
| 2020/0163713 A1* | 5/2020 | Hatcher | A61B 18/18 |
| 2020/0305948 A1* | 10/2020 | Trumer | A61B 18/0218 |

FOREIGN PATENT DOCUMENTS

| | | |
|---|---|---|
| JP | 09257150 A | 9/1997 |
| WO | 2018191013 A1 | 10/2018 |

* cited by examiner

CRYOADHESION APPARATUS

TECHNICAL FIELD

The present invention relates to the field of medical cryoadhesion instruments, and in particular to a cryoadhesion apparatus.

BACKGROUND

Cryoadhesion is commonly used in cryobiopsy, cryocutting, or foreign body removal in the natural lumen of a human body, which has the advantages of large sampling amount, strong adhesion, etc. transluminal cryoadhesion surgeries have been developed more maturely, and a common technique may be, for example, the carbon dioxide throttling cryoadhesion.

In the existing related technology, cryoadhesion devices all adopt a flexible cryoprobe, a main machine, a pedal switch, and a large gas cylinder. During use, a valve in the main machine is opened with the pedal switch to transport a gas such as carbon dioxide from the large gas cylinder to the main machine and then to an inner portion of the flexible cryoprobe, and finally, refrigeration is performed at a needle to cause adhesion with a tissue.

However, a cryoadhesion surgery is usually performed with the assistance of an endoscope (soft), and a doctor holds the endoscope in the left hand and operates a cryoadhesion device with the right hand. The flexible cryoprobe is connected to the main machine, which is connected to the pedal switch and the gas cylinder, and therefore many cables or pipelines need to be added in an operating room. Once a cable or a pipeline causes snagging or is snapped accidentally, potential safety hazards may be caused for a patient and a doctor. In addition, the doctor is required to use both hands and feet, which results in complexity and inconvenience of the surgery. For example, during endoscope operating, a doctor usually needs to move or change a body position, which is apt to lead to an unclear position of the pedal switch. Therefore, the doctor often bows the head to look for the position of the pedal switch.

SUMMARY

The present invention provides a cryoadhesion apparatus, to solve the problems of potential safety hazards and difficult operations.

According to a first aspect of the present invention, a cryoadhesion apparatus is provided, including a remote control assembly, a valve assembly, a needle catheter assembly, and a gas cylinder, where the remote control assembly includes a sheath structure and a remote control mounted in the sheath structure, the sheath structure is provided with a catheter channel for the needle catheter assembly to pass through, and two ends of the valve assembly are respectively connected to the needle catheter assembly and the gas cylinder;

the sheath structure is capable of squeezing the needle catheter assembly, where when squeezing is maintained, the needle catheter assembly is capable of moving along with the sheath structure under a frictional force between an inner wall of the catheter channel and the needle catheter assembly;

the remote control is configured to, when triggered, send a trigger signal to the valve assembly; and the valve assembly is configured to transport, when receiving the trigger signal, gas from the gas cylinder to the needle catheter assembly, to enable the needle catheter assembly to perform freezing.

Optionally, the sheath structure includes a remote control sleeve portion, which is equipped with a trigger part and a remote control chamber configured to accommodate the remote control; and the trigger part is capable of triggering, when touched, a button switch of the remote control in the remote control chamber.

Optionally, the sheath structure further includes a channel base body, the catheter channel is mounted in the channel base body, and the channel base body is fixedly connected to the remote control sleeve portion.

Optionally, the catheter channel in the channel base body includes a guide channel and a squeezing channel, an inner diameter of the squeezing channel is greater than the guide channel, and an inner wall of the squeezing channel is provided with a soft and rough surface; and the inner wall of the squeezing channel is capable of deforming when a corresponding position of the channel base body is pinched, and squeeze the needle catheter assembly.

Optionally, the sheath structure further includes a pressing plate, the catheter channel includes a guide channel, the pressing plate is in rotary connection with the remote control sleeve portion, a side of the pressing plate opposite to the remote control sleeve portion is set up with a squeezing groove, and an outer surface of the remote control sleeve portion is set up with a squeezing surface; the needle catheter assembly is capable of passing between the squeezing groove and the squeezing surface and passing through the guide channel, and the squeezing surface and/or an inner wall of the squeezing groovehave a soft and rough surface;

the pressing plate is configured to, when pressed to rotate, squeeze the needle catheter assembly through the squeezing groove and the squeezing surface; or the pressing plate is configured such that: when the pressing plate is not pressed, the squeezing groove and the squeezing surface squeeze the needle catheter assembly, and when the pressing plate is pressed, the squeezing groove and the squeezing surface no longer squeeze the needle catheter assembly.

Optionally, the sheath structure further includes a pressing plate reset part, the pressing plate reset part is connected between the pressing plate and the remote control sleeve portion and configured to, when the pressing plate is not pressed, drive the pressing plate to rotate to reset, so that the needle catheter assembly is no longer squeezed or is squeezed.

Optionally, an inner wall of the guide channel is provided with a rigid and smooth surface.

Optionally, at least one of the sheath structure, the remote control and the needle catheter assembly is disposable.

Optionally, the valve assembly includes an electromagnetic valve and a receiving circuit board, and the electromagnetic valve includes a pin, a pin tube, a pin reset part, a seat, and a pin driving structure; an intake channel is provided inside the pin, the pin passes through the pin tube, an end of the pin tube is configured to be connected to the needle catheter assembly, another end of the pin tube is connected to a side of the seat, and another side of the seat is connected to the gas bottle; an end of the pin is connected to the needle catheter assembly;

the pin driving structure is configured to, when the receiving circuit board receives the trigger signal, drive the pin to be in an intake position, at which the pin is capable of being inserted into the gas cylinder, so that the gas in the gas bottle enters the intake channel and flows through the intake channel to the needle catheter assembly; and the pin reset part is configured to, when the pin driving structure does not drive the pin, drive the pin to reset from the intake position to a non-intake position, at which the pin is not inserted into the gas cylinder.

Optionally, the pin includes a first pin section, a second pin section, a third pin section, and a fourth pin section that are sequentially connected; the first pin section is inserted into the intake chamber of the needle catheter assembly; the fourth pin section is inserted into the gas cylinder; and an outer diameter of the third pin section matches an inner diameter of the pin tube, an outer diameter of the second pin section is less than an outer diameter of the third pin section, and the pin reset part is disposed on an outer side of the second pin section.

Optionally, a side wall of the fourth pin section is provided with an intake vent, and when the pin is inserted into the gas cylinder, the gas enters the intake channel from the intake vent.

Optionally, an inner side of the pin tube is fixedly provided with a pin limit portion, and the pin reset part is connected to the pin limit portion; and the pin limit portion is capable of blocking an end of the third pin section that is far away from the gas bottle, and the pin reset part is located at the outer side of the second pin section to limit a motion position of the pin when reset.

The pin limit portion includes at least two fan-shaped limit portions, which are arranged at an interval along a circumferential direction of the pin to form a pressure relief gap between two adjacent fan-shaped limit portions;

the third pin section is provided with a pressure relief groove running through two ends of the third pin section; and when the pin is not inserted into the gas bottle, the gas in the intake channel sequentially flowing through the intake vent, the pressure relief groove, and the pressure relief gap to be discharged to a compartment between the second pin section and an inner wall of the pin tube.

Optionally, the outer side of the second pin section is provided with a pin outer thread, which matches and is connected to a limit nut, and the pin reset part is connected to the limit nut; and the limit nut is capable of adjusting a position of the limit nut relative to the pin by rotating relative to the pin outer threads, to change a compression amount or an expansion amount of the pin reset part.

Optionally, the needle catheter assembly includes a needle, a catheter, and a connector structure that are sequentially connected, an intake tube is provided inside the catheter, the connector structure is connected to the valve assembly and is capable of transporting the gas from the valve assembly to the intake tube through which the gas is transported to the needle, and the catheter passes through the catheter channel.

Optionally, the connector structure includes a connector body, a connecting portion, and a head tube; an intake chamber is provided inside the connector body; the connecting portion and the head tube are respectively disposed on two ends of the connector body; and the intake chamber is configured for the pin of the valve assembly to be inserted after passing through the connecting portion, the intake tube passes through the head tube to be connected to the intake chamber, and the connecting portion is configured to be butt-jointed with the pin tube in the valve assembly.

Optionally, the valve assembly further includes a valve housing, and the electromagnetic valve and the receiving circuit board are disposed inside the valve housing; the valve housing is provided with a first exhaust vent and a second exhaust vent;

the connecting portion is provided with a pressure relief vent, an end of the pressure relief vent is in communication to a compartment between the pin and an inner wall of the pin tube, and another end of the pressure relief vent is in direct or indirect communication to the first exhaust vent in the valve assembly; and when the pin is not inserted into the gas bottle, the gas discharged to the compartment between the pin and the inner wall of the pin tube is capable of sequentially flowing through the pressure relief vent, the first exhaust vent, and an inner cavity of the valve housing to be discharged to the second exhaust vent.

Optionally, the valve assembly further includes a valve housing, and the electromagnetic valve and the receiving circuit board are disposed inside the valve housing; the valve housing is provided with a first exhaust vent and a second exhaust vent;

the needle catheter assembly further includes a return pipe and a connector housing, the connector structure is disposed inside the connector housing, the connector housing is provided with a connector exhaust vent, the return pipe is connected between the catheter and the connector structure, disposed around an outer side of the intake tube, and in communication to the compartment between the catheter and the intake tube, and a pipe wall of the return pipe is provided with a return vent; and the gas returning to the compartment between the catheter and the intake tube is capable of sequentially flowing through the return pipe, the return vent, an inner cavity of the connector housing, the connector exhaust vent, the first exhaust vent, and an inner cavity of the valve housing to be discharged to the second exhaust vent.

In the cryoadhesion apparatus provided in the present invention, since the needle catheter assembly passes through the catheter channel of the remote control assembly, the control of freezing and the push-in/pull-out of the catheter can both be achieved based on the remote control assembly, thereby making it convenient for an operator to perform the control of freezing and the push-in/pull-out of the catheter with one hand, and avoiding the use of a pedal, a main machine, or the like. Therefore, the operation of a transluminal cryoadhesion surgery is simplified, and the convenience and safety of the surgery are improved. In addition, in a case in which no parts such as a pedal switch are configured while an electromagnetic valve is used, space can be effectively saved.

BRIEF DESCRIPTION OF DRAWINGS

To explain the embodiments of the present invention or the technical solutions in the prior art more clearly, the accompanying drawings required for the description of the embodiments or the prior art will be briefly described below. Apparently, the accompanying drawings in the following description are only some embodiments of the present invention, and a person of ordinary skill in the art may further derive other drawings based on these accompanying drawings without creative efforts.

REFERENCE NUMERALS

Figure 1:
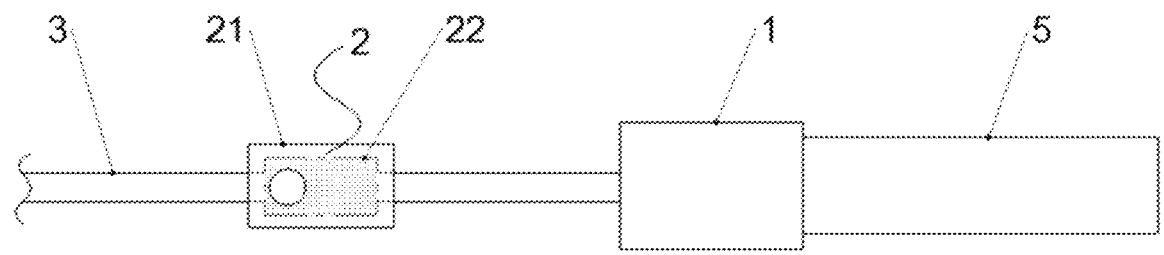
FIG. 1 is a schematic diagram illustrating a configuration of a cryoadhesion apparatus according to an embodiment of the present invention.

1—Valve assembly;
11—Electromagnetic valve;
111—Pin;
1111—Intake channel;
1112—Intake vent;
1113—Pressure relief groove;
1114—Sealing ring groove;
1115—First pin section;
1116—Second pin section;
1117—Third pin section;
1118—Fourth pin section;
112—Seat;
113—Pin tube;
1131—Pin limit portion;
114—Pin reset part;
115—Limit nut;
116—Electromagnetic coil;
117—Electromagnetic valve housing;
118—Fixing nut;
119—Sealing ring;
12—Receiving circuit board;
121—Valve button;
13—Valve housing;
131—First exhaust vent;
132—Second exhaust vent;
133—Semi-housing;
2—Remote control assembly;
21—Sheath structure;
2101—Squeezing channel;
2102—Guide channel;
2103—Remote control chamber;
2104—Remote control button;
2105—Lower elastic sheet groove;
2106—Remote control sleeve portion;
2107—Channel base body;
2108—Female rotary articulation;
2109—Squeezing surface;
2110—Pressing plate;
2111—Squeezing groove;
2112—Male rotary articulation;
2113—Pressing plate reset part;
22—Remote control;
221—Remote control casing;
222—Transmitting circuit board;
2221—Button switch;
2222—Protection switch;
223—Button battery;
224—Battery cover;
3—Needle catheter assembly;
31—Needle;
32—Catheter;
33—Return pipe;
331—Return vent;
34—Front squeezing tube;
35—Rear squeezing tube;
36—Intake tube;
37—Connector structure;
371—Head tube;
372—Intake chamber;
373—Connecting portion;
374—Pressure relief vent;
375—Connector body;
38—Connector housing;
39—Bending-proof member;
4—Battery pack;
5—Gascylinder;
51—Gas cylinder outlet;
511—Front sealing structure;
512—Rear sealing structure;
6—Gas cylindercover; and
61—Tail exhaust vent.

DESCRIPTION OF EMBODIMENTS

The following clearly and completely describes the technical solutions in the embodiments of the present invention with reference to the accompanying drawings in the embodiments of the present invention. Apparently, the embodiments described are merely some embodiments, other than all embodiments, of the present invention. All other embodiments derived based on the embodiments of the present invention by a person of ordinary skill in the art without creative efforts shall fall within the protection scope of the present invention.

The terms "first", "second", "third", "fourth," and the like, if existent, in the specification, claims, and the accompanying drawings of the present invention are used to distinguish between similar objects and are not intended to describe a particular order or sequence. It should be understood that the terms used in such a way are interchangeable where appropriate, so that the embodiments of the present invention described herein are practicable in order other than those illustrated or described herein. In addition, the terms "comprise" and "have" and any variations thereof are intended to cover a non-exclusive inclusion, for example, a process, method, system, product or device including a series of steps or units is not necessarily limited to those steps or units that are expressly listed, but may include other steps or units that are not expressly listed or are inherent to the process, method, product, or device.

The technical solutions of the present invention are described in detail below with specific embodiments. The following specific embodiments may be combined with each other, and the same or similar concepts or processes may not be repeated in some embodiments.

Figure 2:
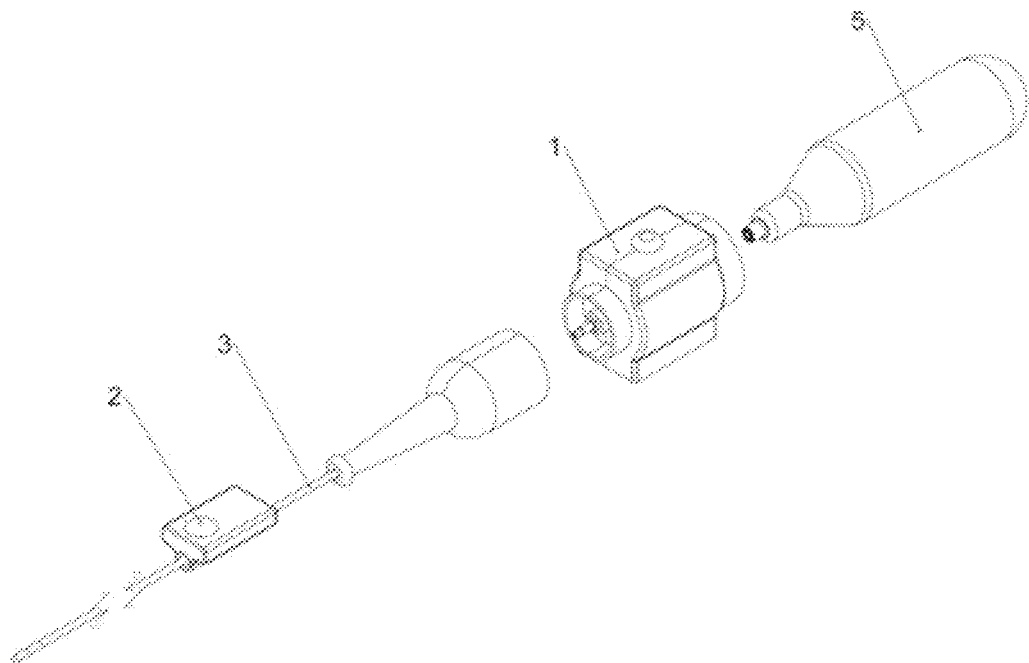
FIG. 2 is schematic structural diagram 1 of a cryoadhesion apparatus according to an embodiment of the present invention.
Figure 3:
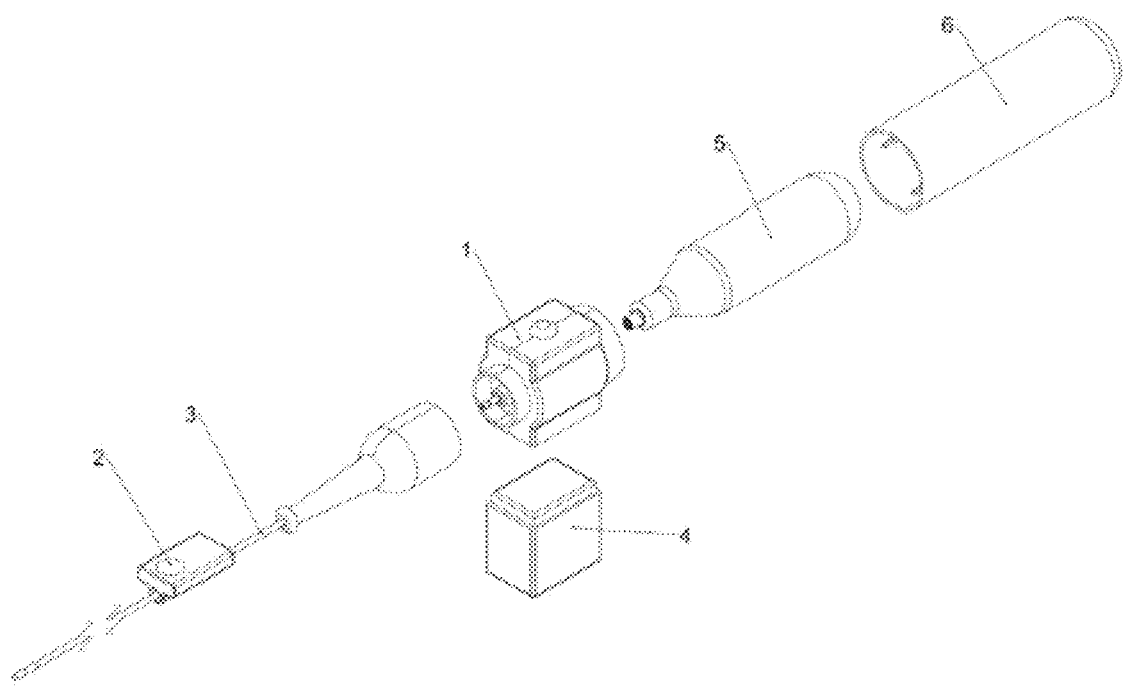
FIG. 3 is schematic structural diagram 2 of a cryoadhesion apparatus according to an embodiment of the present invention.

FIG. 1 is a schematic diagram illustrating a configuration of a cryoadhesion apparatus according to an embodiment of the present invention. FIG. 2 is schematic structural diagram 1 of a cryoadhesion apparatus according to an embodiment of the present invention. FIG. 3 is schematic structural diagram 2 of a cryoadhesion apparatus according to an embodiment of the present invention.

Referring to FIG. 1 to FIG. 3, the cryoadhesion apparatus includes: a remote control assembly 2, a valve assembly 1, a needle catheter assembly 3, and a gas cylinder 5.

The remote control assembly 2 includes a sheath structure 21 and a remote control 22 mounted in the sheath structure 21, the sheath structure 21 is provided with a catheter channel for the needle catheter assembly to pass through, and two ends of the valve assembly 1 are respectively connected to the needle catheter assembly 3 and the gas bottle 5.

The sheath structure 21 is capable of squeezing the needle catheter assembly 3 (for example, the sheath structure 21 may be controlled to perform squeezing when an operator performs manipulation or the squeezing occurs when the sheath structure 21 is not manipulated). When the squeezing is maintained, the needle catheter assembly 3 is capable of moving along with the sheath structure 21 under a frictional force between an inner wall of the catheter channel and the needle catheter assembly 3.

It can be seen that the squeezing can be understood as squeezing in which the frictional force generated by the squeezing can cause the two to move together, and a generating principle and mode of the squeezing can be arbitrary. For example, the squeezing may be generated due to deformation in at least part of the sheath structure 21, or may be generated due to a movement of at least part of the sheath structure 21. In any case, the solution does not depart from the description of this embodiment.

The remote control 22 is configured to, when triggered, send a trigger signal to the valve assembly 1.

The valve assembly 1 is configured to transport, when receiving the trigger signal, a gas from the gas cylinder to the needle catheter assembly 3, to enable the needle catheter assembly 3 to perform freezing.

The performing of freezing can be understood as generating a refrigeration capacity by throttling through a Joule-Thomson effect in a case in which a gas is transported to perform cryoadhesion of tissues outside an outer portion of the needle in the needle catheter assembly 3.

The trigger signal may be a signal of any form and content and does not depart from the description of this embodiment, so long as the valve assembly 1 can recognize and perform transporting of a gas in response to the signal to achieve freezing. The trigger signal may be transmitted wirelessly, for example, transmitted in a wireless manner, but a wired transmission solution is not completely excluded. Either way, the use of both hands and feet for joint operation can be avoided, and it is convenient to implement the control of freezing and the push-in and pull-out of a catheter with one hand.

It can be seen that, in the solutions mentioned in this embodiment, the needle catheter assembly passes through the catheter channel of the remote control assembly, and further the control of freezing and the push-in/pull-out of the catheter can both be achieved based on the remote control assembly, thereby making it convenient for an operator to achieve the control of freezing and the push-in/pull-out of the catheter with one hand. Therefore, the operation of a transluminal cryoadhesion surgery is simplified, and the convenience and safety of the surgery are improved. In addition, in a case in which no parts such as a pedal switch are configured while an electromagnetic valve is used, space can be effectively saved.

Figure 4:
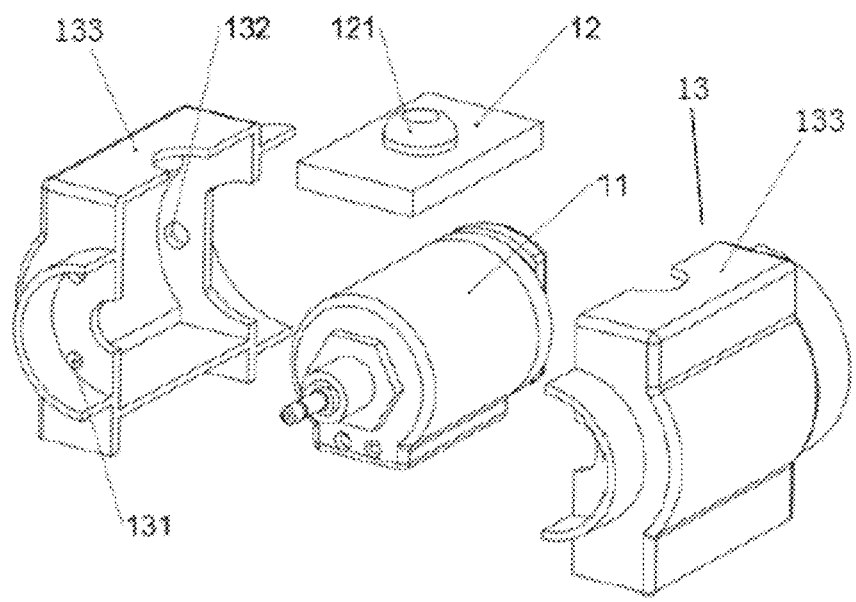
FIG. 4 is a schematic structural diagram of a valve assembly according to an embodiment of the present invention.
Figure 5:
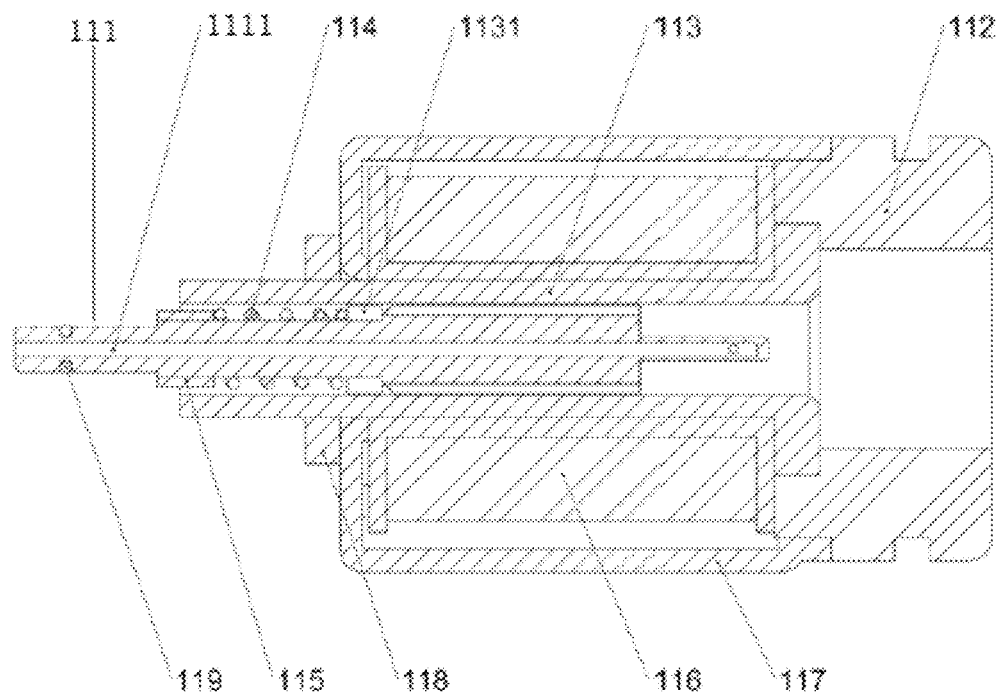
FIG. 5 is a cross-sectional view of an electromagnetic valve according to an embodiment of the present invention.
Figure 6:
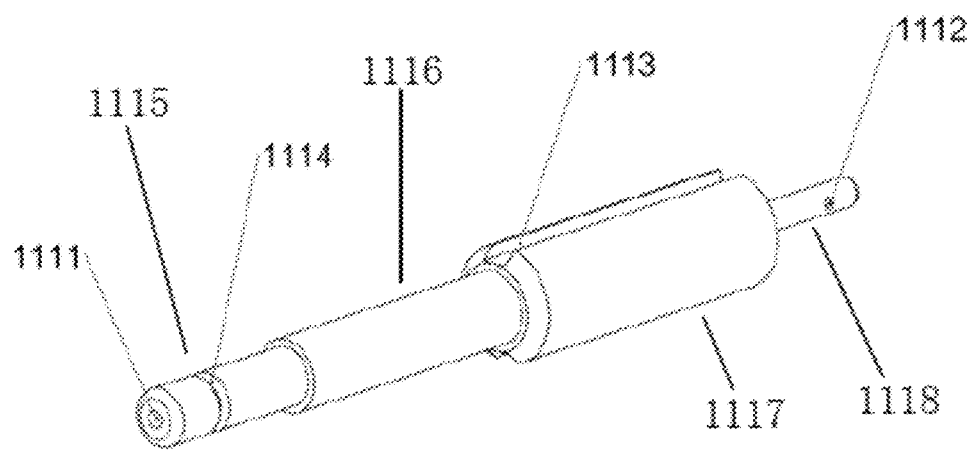
FIG. 6 is a schematic structural diagram of a pin according to an embodiment of the present invention.

FIG. 4 is a schematic structural diagram of a valve assembly according to an embodiment of the present invention. FIG. 5 is a cross-sectional view of an electromagnetic valve according to an embodiment of the present invention. FIG. 6 is a schematic structural diagram of a pin according to an embodiment of the present invention.

Referring to FIG. 4 to FIG. 6, the valve assembly 1 includes an electromagnetic valve 11 and a receiving circuit board 12.

The electromagnetic valve 11 includes a pin 111, a pin tube 113, a pin reset part 114, a seat 112, and a pin driving structure. An intake channel 1111 is provided inside the pin 111, the pin 111 passes through the pin tube 113, an end of the pin tube 113 is configured to be connected to the needle catheter assembly 3, another end of the pin tube 113 is connected to a side of the seat 112, and another side of the seat 112 is connected to the gas bottle 5. An end of the pin 111 is connected to the needle catheter assembly 3.

The pin driving structure is configured to, when the receiving circuit board 12 receives the trigger signal, drive the pin 111 to be in an intake position.

The driving herein may specifically indicate: in a case in which the trigger signal is received, if the pin 111 is located at the intake position, the pin driving structure may drive the pin 111 to be kept in the intake position, or if the pin 111 is not located at the intake position, the pin driving structure may drive the pin 111 to move to the intake position. In addition, the pin driving structure may perform the foregoing driving under the control of the receiving circuit board 12.

The intake position herein can be understood as: a position at which the pin 111 is capable of being inserted into the gas cylinder 5, so that the gas from the gas cylinder 5 enters the intake channel 1111 and is transported through the intake channel to the needle catheter assembly.

The pin reset part is configured to, when the pin driving structure does not drive the pin 111, drive the pin 111 to reset from the intake position to a non-intake position, at which the pin is not inserted into the gas cylinder.

Further, a sealing structure (for example, a rear sealing structure 512) for sealing off a gas cylinder outlet may be disposed in the gas cylinder 5, so that the sealing structure no longer seals off the gas cylinder outlet when the pin 111 enters the gas cylinder 5 and further the pin 111 can be inserted into the gas cylinder 5 to obtain the gas from the gas cylinder and to transmit the gas, and that the seal structure may alternatively again seal off the gas cylinder outlet under the driving of a corresponding reset part when the pin 111 is reset.

The above-mentioned non-intake position can be understood as any position at which the pin 111 is not inserted into the gas cylinder, or the pin 111 does not forces open a sealing.

The electromagnetic valve 11 and/or the receiving circuit board 12 may be powered by a battery pack 4. The battery pack 4 may be a rechargeable battery pack, which may then be detached and charged separately, or the battery pack 4 may be a non-rechargeable battery pack.

In an implementation shown in FIG. 5, a movement of the pin 111 is a linear movement, and the pin 111 may move in an axial direction of the pin tube 113. In other optional implementations, a movement of the pin 111 may alternatively be an arc movement, a curved movement, or the like.

The electromagnetic valve 11 is used in the implementation shown in the figure, and therefore the pin driving structure may include an electromagnetic coil 116 which can generate a required electromagnetic force when energized, and further, the pin 111 may move under the driving of the electromagnetic force (for example a movement from the left to the right as shown in FIG. 5). The electromagnetic coil 116 may be mounted in a corresponding electromagnetic valve housing 117, a position of which may be secured relative to the seat 112 and the pin tube 113. For example, the electromagnetic valve housing 117 may be secured to the seat 112 by screwing a fixing nut 118 to a threaded portion of an outer side at a front end of the pin tube 113.

In other optional implementations, valve devices employing other principles other than the electromagnetic valve 11 are not excluded.

The pin reset part can be understood as any part capable of being deformed (for example, curved, pulled up, compressed, or bent) by an external force and capable of generating a reset force when the external force is removed. In an example, the pin reset part can adopt a spring. When the pin enters an intake position, the spring may be expanded or compressed, and then when a force (such as an electromagnetic force) that drives the pin in the intake position disappears, the pin reset part may drive the pin out of the intake position and into the non-intake position.

In an implementation, referring to FIG. 5 and FIG. 6, the pin 111 includes a first pin section 1115, a second pin section 1116, a third pin section 1117, and a fourth pin section 1118 that are sequentially connected, which may be the four sections of different diameters in FIG. 6.

The first pin section 1115 is inserted into an intake chamber 372 of the needle catheter assembly 3, and in addition, a dynamic sealing may be achieved between the first pin section 1115 and the intake chamber 372. In an example, an outer side of the first pin section 1115 may be provided with a sealing ring 119. The sealing ring 119 may be disposed in an annular sealing ring groove 1114 on an outer side of the first pin section 1115.

Optionally, the fourth pin section 1118 is configured to be inserted into the gas cylinder 5, where a side wall of the fourth pin section 1118 is provided with an intake vent 1112, and when the pin 111 is inserted into the gas cylinder 5, gas is capable of entering the intake channel 1111 from the intake vent 1112. The number, dimension, and arrangement of the intake vent 1112 may be arbitrary without being limited to those shown in FIG. 6.

An outer diameter of the third pin section 1117 matches an inner diameter of the pin tube 113, and further the pin 111 moves along an inner wall of the pin tube 113 through the third pin section 1117, thereby achieving a guiding function.

An outer diameter of the second pin section 1116 is less than the outer diameter of the third pin section 1117, and the pin reset part 114 is disposed on an outer side of the second pin section 1116. It can be seen that by using the second pin section 1116, space can be provided for a movement of the pin reset part 114.

A dimensional relationship of the pin sections (such as lengths and the outer diameters) may be shown in FIG. 6, or may be other dimensional relationships and shapes, as long as the above requirements can be met, all of which do not depart from the description of this embodiment.

Referring to FIG. 5, in one of the implementations, an inner side of the pin tube 113 is fixedly provided with a pin limit portion 1131, and the pin reset part 114 is connected to the pin limit portion 1131. For example, when the pin reset part 114 is a spring, an end of the spring may be connected to the pin limit portion 1131.

The pin limit portion 1131 is capable of blocking an end of the third pin section 1117 that is far away from the gas bottle 5, and the pin reset part 1131 is located at the outer side of the second pin section to limit a motion position of the pin when reset.

Specifically, by way of example of FIG. 5, under an action of an electromagnetic force, the pin 111 moves to the right in the figure and enters the intake position, in which case, the spring may be compressed. After the electromagnetic force disappears, the spring may generate a leftward force acting on the pin to enable the pin to move leftward. When the pin moves to a limit position, a front end of the third pin section 1117 may press against the pin limit portion 1131 so that the pin limit portion 1131 is limited.

In a specific implementation process, the pin limit portion 1131 includes at least two fan-shaped limit portions, which are arranged at an interval along a circumferential direction of the pinto form a pressure relief gap between two adjacent fan-shaped limit portions.

Referring to FIG. 6, in a specific implementation process, the third pin section 1117 is provided with a pressure relief groove 1113 running through two ends of the third pin section 1117.

When the pin 111 is not inserted into the gas cylinder 5, that is, when the pin 111 is not in the intake position, the gas in the intake channel 1111 is capable of sequentially flowing through the intake vent 1112, the pressure relief groove 1113, and the pressure relief gap to be discharged to a compartment between the second pin section 1116 and an inner wall of the pin tube 113, where the compartment may form part of a passage for rapid gas discharge.

Through the foregoing electromagnetic valve, rapid opening and rapid intake pressure relief of the gas bottle can be implemented by using the pin. For example, when the remote control is pressed, freezing is achieved, and when released, gas discharge is implemented, to implement gas discharge and rewarming.

Referring to FIG. 5, in one of the implementations, an outer side of the second pin section 1116 is provided with pin outer threads, which match and are connected to a limit nut 115, and the pin reset part 114 is connected to the limit nut 115. It can be seen that when the pin reset part 114 is a spring, an expansion and compression direction of the spring may be an axial direction of the pin and the pin tube, and the spring is connected to the limit nut 115 and pin limit portion 1131 along the axial direction.

The limit nut 115 is capable of adjusting a position of the limit nut 115 relative to the pin 111 by rotating relative to a pin outer thread to change a compression amount or an expansion amount of the pin reset part 114.

In addition, in the example shown in FIG. 5, under an action of an electromagnetic force, a movement of the pin may enable the spring to be compressed. In other examples, for example, when the limit nut is located at the left side of the spring and is fixedly connected to the pin tube 113, and another fixing portion is fixedly connected to the pin 111 and located at the right side of the spring, under the action of the electromagnetic force, the movement of the pin may enable the spring to be expanded. In any case, the solution does not depart from the description of this embodiment.

In one of the implementations, referring to FIG. 4, the valve assembly 1 further includes a valve housing 13, and the electromagnetic valve 11 and the receiving circuit board 12 are disposed inside the valve housing 13.

In an example, the receiving circuit board 12 may be provided with a valve button 121, which may be externally communicated through a through hole in the valve housing 13 to be adapted to be manipulated. The valve button 121 may be used as a standby button, configured to start freezing by pressing the valve button 121 when the remote control is inoperative.

The valve housing 13 may include two semi-housings 133, which may be connected by snaps or screws, and sealing measures may be taken at seams.

The valve housing 13 may further be provided with a first exhaust vent 131 and a second exhaust vent 132, which may be respectively regarded as a front exhaust vent and a rear exhaust vent that may be used to guide a gas to be discharged backward. Specifically, the gas may be discharged to the gas cylinder cover 6 through the second exhaust vent 132 after entering an inner cavity through the first exhaust vent 131. For example, the gas may be discharged through a tail exhaust vent 61 of the gas cylinder cover 6. The vents may be used for discharging of a returned gas, or may be used for rapid gas discharging after intake stops.

In addition, the valve housing 13 may further be provided with a remote control holding recess, so that the remote control assembly 2 or the remote control 22 in the remote control assembly 2 may be placed in the remote control holding recession the valve housing 13. In another solution, the remote control assembly 2 or the remote control 22 in the remote control assembly 2 may alternatively be suspended or attached to the valve assembly to prevent the remote control from being lost.

A power supply of the above-mentioned electromagnetic valve and receiving circuit board may be provided by a battery pack, or may be achieved by being connected to a socket through a cable. Further, the cable may directly provide an alternating current, or a rectifier circuit may alternatively be configured in the cable to convert an alternating current into a direct current for supply to the electromagnetic valve and the receiving circuit board.

Figure 7:
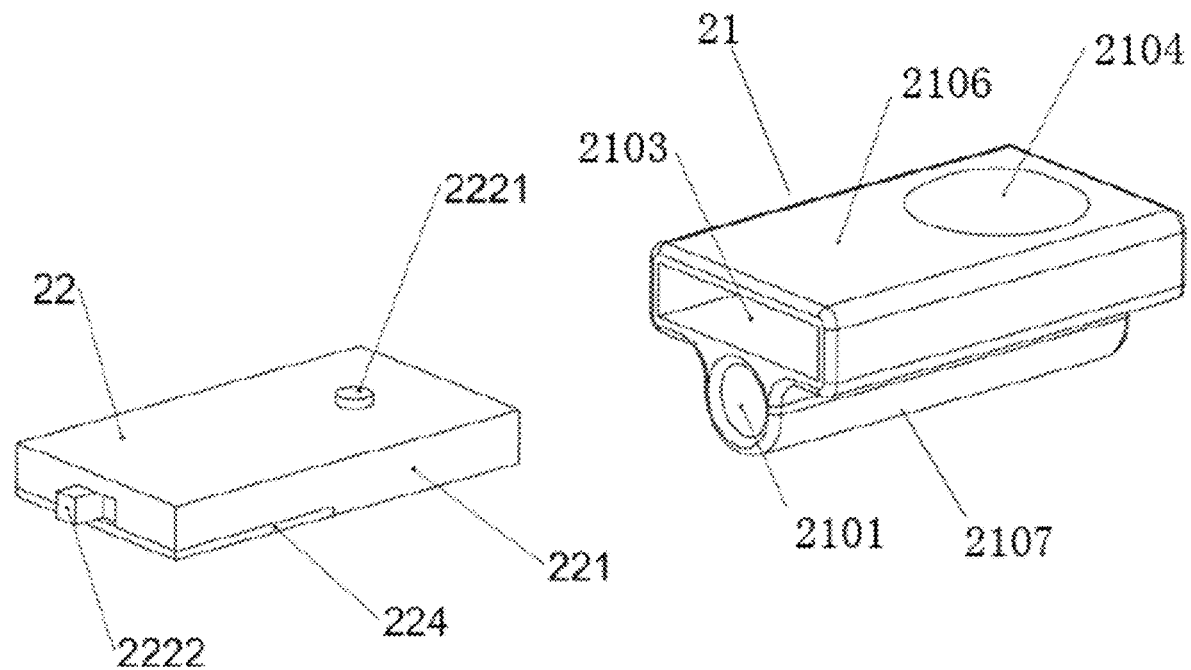
FIG. 7 is schematic structural diagram 1 of a sheath structure and a remote control according to an embodiment of the present invention.
Figure 8:
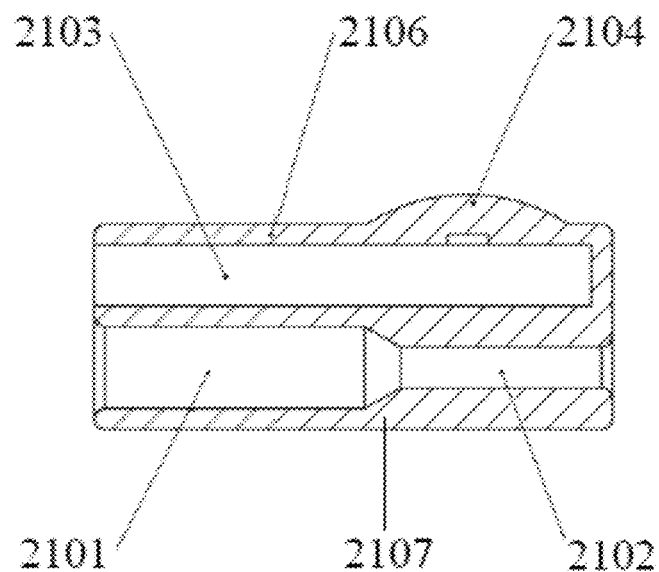
FIG. 8 is cross-sectional view 1 of a sheath structure according to an embodiment of the present invention.
Figure 9:
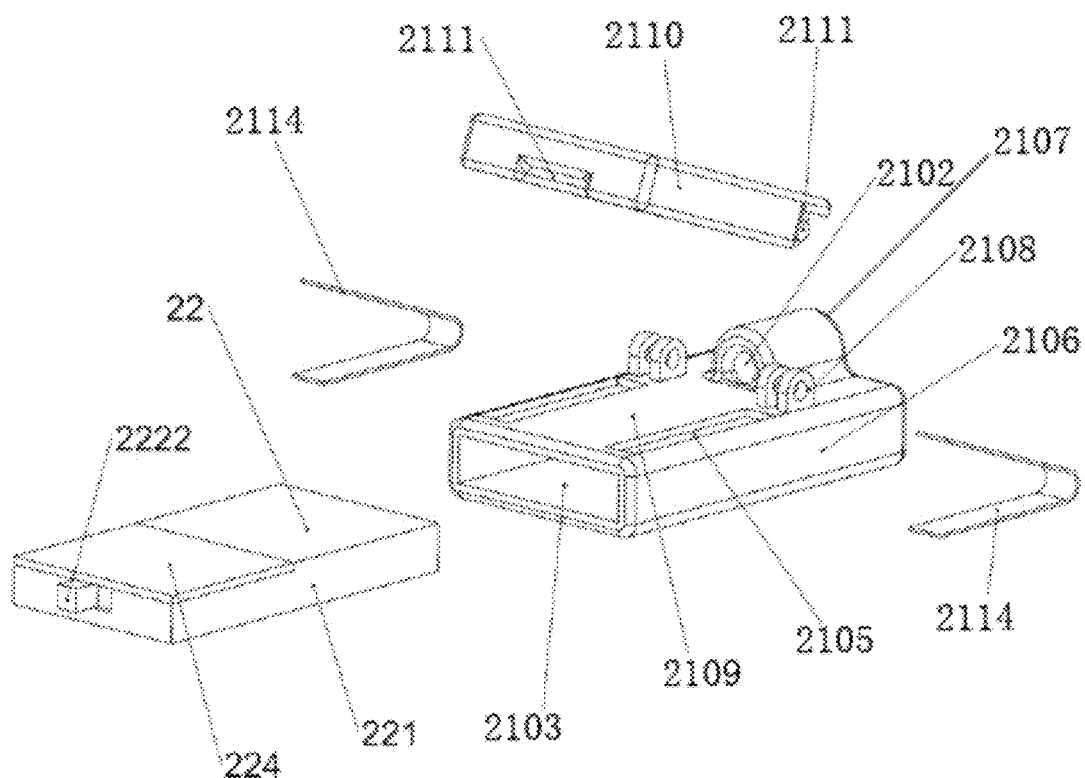
FIG. 9 is schematic structural diagram 2 of a sheath structure and a remote control according to an embodiment of the present invention.
Figure 10:
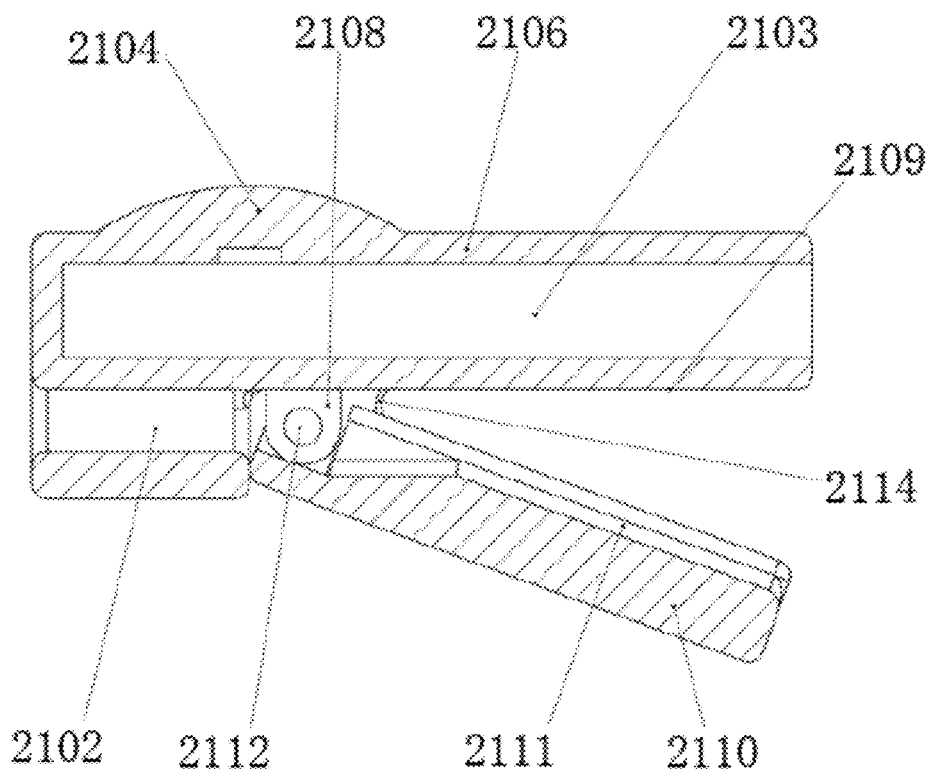
FIG. 10 is cross-sectional view 2 of a sheath structure according to an embodiment of the present invention.

FIG. 7 is schematic structural diagram 1 of a sheath structure and a remote control according to an embodiment of the present invention. FIG. 8 is cross-sectional view 1 of a sheath structure according to an embodiment of the present invention. FIG. 9 is schematic structural diagram 2 of a sheath structure and a remote control according to an embodiment of the present invention. FIG. 10 is cross-sectional view 2 of a sheath structure according to an embodiment of the present invention.

Referring to FIG. 7 to FIG. 10, the sheath structure 21 includes a remote control sleeve portion 2106, which is provided with a trigger part (for example, the remote control button 214 shown in the figures) and a remote control chamber 2103 configured to accommodate the remote control 22. The trigger part is capable of triggering, when touched, a button switch 2221 of the remote control 22 in the remote control chamber 2103.

By the foregoing solution, accommodating mounting of the remote control 22 relative to the sheath structure 21 can be achieved.

In one of the implementations, the sheath structure 21 further includes a channel base body 2107. The catheter channel is disposed in the channel base body 2107, and the channel base body 2107 is fixedly connected to the remote control sleeve portion 2106. Specifically, the catheter channel and the channel base body may be of an integrated structure or may be installed together.

In the implementations shown in FIG. 7 and FIG. 8, the catheter channel in the channel base body 2107 includes a guide channel 2102 and a squeezing channel 2101. An inner diameter of the squeezing channel 2101 is greater than the guide channel, and in addition, an inner diameter of the guide channel 2102 may be greater than an outer diameter of the catheter in the needle catheter assembly 3.

The inner wall of the squeezing channel 2101 is capable of deforming when a corresponding position of the channel base body 2107 is pinched and squeezing the needle catheter assembly 3.

The inner wall of the squeezing channel 2101 may be provided with a soft and rough surface. For example, the inner wall of the squeezing channel 2101 may be provided with a soft and rough material of rubber or silica, and/or, a corresponding portion of the channel base body 2107 and the remote control sleeve portion 2106 may adopt a soft and rough material of rubber or silica. By the soft and rough design, a frictional force with the catheter can be increased, thereby facilitating manipulation.

By the guide channel 2102, the catheter 32 is guided to a required direction to prevent bending. Specifically, an inner wall of the guide channel 2102 may be provided with a rigid and smooth surface, so that smoothness of the catheter 32 sliding in the guide channel 2102 can be increased, thereby ensuring a low resistance movement of the needle catheter assembly 3.

It can be seen that, in the implementations shown in FIG. 7 and FIG. 8, a movement of the remote control assembly 2 together with the needle catheter assembly 3 may be achieved by way of pinching, in this way the entire sheath structure 21 may be disposable, and in an example, the entire remote control assembly 2 may alternatively be disposable.

In the implementations shown in FIG. 9 and FIG. 10, the sheath structure 21 further includes a pressing plate 2110, the catheter channel includes a guide channel 2102, and as shown previously, the guide channel 2102 is also disposed in the channel base body 2107.

The pressing plate 2110 is in rotary connection with the remote control sleeve portion 2106. For example, the remote control sleeve portion 2106 and the pressing plate 2110 may be connected by using a female rotary articulation 2108 and a male rotary articulation 2112. The pressing plate 2110 may rotate around the articulation by an angle of a certain degree.

A side of the pressing plate 2110 opposite to the remote control sleeve portion 2106 is provided with a squeezing groove 2111. An outer surface of the remote control sleeve portion 2106 is provided with a squeezing surface 2109. The needle catheter assembly 3 (for example, a catheter thereof) is capable of passing between the squeezing groove 2111 and the squeezing surface 2109 and passing through the guide channel 2102.

The pressing plate 2110 is configured to, when pressed to rotate, squeeze the needle catheter assembly through the squeezing groove 2111 and the squeezing surface 2109.

The squeezing surface 2109 and/or the inner wall of the squeezing groove 2111 is provided with a soft and rough surface, for example, adopting a soft and rough silica material.

In addition, similar to the implementations shown in FIG. 7 and FIG. 8, an inner wall of the guide channel 2102 in this implementation may likewise be provided with a rigid and smooth surface previously mentioned.

Referring to FIG. 9 and FIG. 10, the sheath structure 1 further includes a pressing plate reset part 2113, the pressing plate reset part 2113 is connected between the pressing plate 2110 and the remote control sleeve portion 2106 and configured to, when the pressing plate 2110 is not pressed, drive the pressing plate 2110 to rotate to reset, so that the needle catheter assembly is no longer squeezed.

In an example, the pressing plate reset part 2113 may be, for example, an elastic sheet, which may be placed on an upper elastic sheet groove (not shown) and a lower elastic sheet groove 2105 disposed on the pressing plate 2110.

In the foregoing solution, the needle catheter assembly 3 is inserted into the guide channel 2102. By pressing the pressing plate 2110 with a finger, the pressing plate reset part 2113 may be compressed, and the needle catheter assembly 3 will be pressed between the squeezing groove 2111 and the squeezing surface 2109 and unable to move. In this case, the needle catheter assembly 3 can be pushed in and pulled out. When the pressing plate 2110 is released, the pressing plate 2110 may rotate (that is, become upturned) under the action of an elastic force of the pressing plate reset part 2113, and the needle catheter assembly 3 (for example, the catheter 32 thereof) is restored to a free moving state.

In the solutions shown in FIG. 9 and FIG. 10, the needle catheter assembly 3 can move freely in a natural state, and after the pressing plate is pressed, the needle catheter assembly 3 is squeezed and secured. In other optional solutions, it may also be configured such that the needle catheter assembly 3 is squeezed and secured in a natural state, and after the pressing plate is pressed, the catheter can move freely.

It can be seen that, in other implementations, the pressing plate 2110 is configured such that: when the pressing plate 2110 is not pressed, the squeezing groove 2111 and the squeezing surface 2109 squeeze the needle catheter assembly 3, and when the pressing plate is pressed, the squeezing groove and the squeezing surface no longer squeeze the needle catheter assembly. Correspondingly, the pressing plate reset part 2113 is configured to, when the pressing plate 2110 is not pressed, drive the pressing plate 2110 to rotate to reset, so that the needle catheter assembly 3 squeezed.

In a specific implementation process, no matter which method is adopted to achieve squeezing, at least one of the entire sheath structure, the remote control and the needle catheter assembly is disposable.

Figure 11:
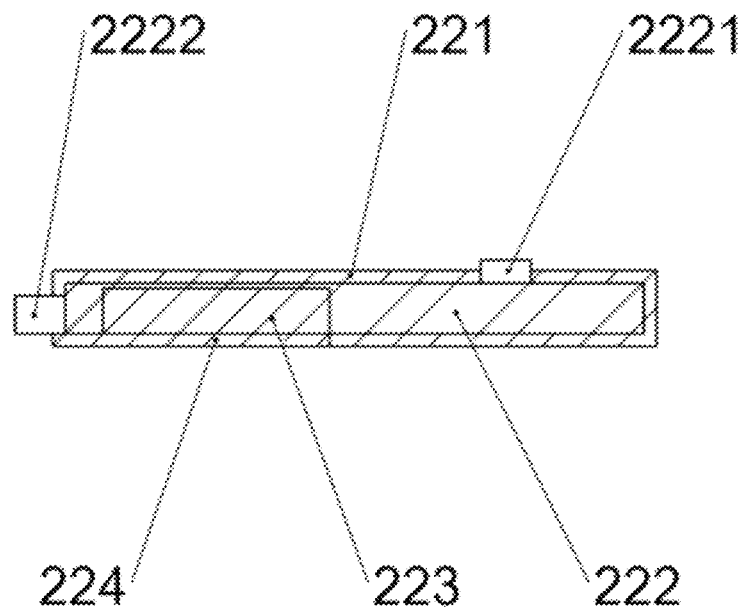
FIG. 11 is a cross-sectional view of a remote control according to an embodiment of the present invention.

FIG. 11 is a cross-sectional view of a remote control according to an embodiment of the present invention.

Referring to FIG. 11, the remote control 22 may include a transmitting circuit board 222, a button battery 223, and a remote control casing 221. The transmitting circuit board 222 and the button battery 223 are placed in the remote control casing 221. The remote control casing 221 may be provided with a battery cover 224, the button battery 223 may be disposed in a corresponding position of the battery cover 224, and the battery cover may be used for changing the button battery 223.

The transmitting circuit board 222 may be configured with the above-mentioned button switch 2221, and may further be configured with a protection switch 2222. The protection switch 2222 may be configured to turn on and off the transmitting circuit board of the remote control 22, so that the button switch 2221 of the transmitting circuit board 222 does not act correspondingly after being touched. The button switch 2221 is configured to be touched when a remote control button 2104 is pressed, and after the button switch 2221 is touched, the transmitting circuit board may send a trigger signal. In this solution, by turning off the protection switch 2222, the remote control button 2104 can be prevented from being mistouched by mistake (that is, the button switch 2221 is prevented from being triggered by mistake).

Figure 12:
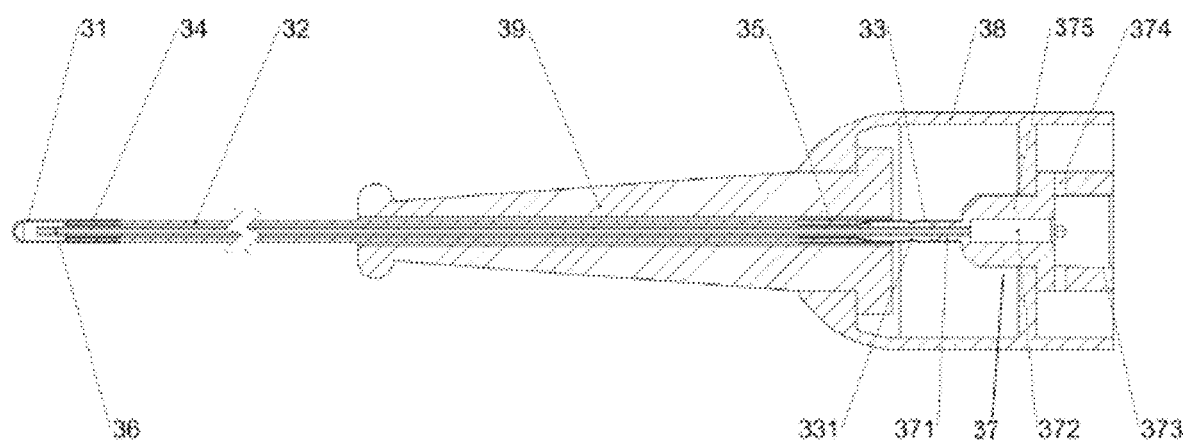
FIG. 12 is a cross-sectional view of a needle catheter assembly according to an embodiment of the present invention.

FIG. 12 is a cross-sectional view of a needle catheter assembly according to an embodiment of the present invention.

Referring to FIG. 12, the needle catheter assembly 3 includes a needle 31, a catheter 32, and a connector structure 37 that are sequentially connected. An intake tube 36 is provided inside the catheter. The connector structure 37 is connected to the valve assembly 1 and is capable of transporting the gas from the valve assembly 1 (for example, from the intake channel 1111 thereof) to the intake tube 36 through which the gas is transported to the needle 31. The catheter 32 passes through the catheter channel.

In one of the implementations, the connector structure 37 may include a connector body 375, a connecting portion 373, and a head tube 371. An intake chamber 372 is provided inside the connector body 375. The connecting portion 373 and the head tube 371 are respectively disposed at two ends of the connector body 375.

The intake chamber 372 is configured for the pin of the valve assembly to pass through the connecting portion to be inserted, and in addition, a dynamic sealing can be achieved. The intake tube 36 passes through the head tube 371 to be connected to the intake chamber 372. Specifically, the intake tube 36 is placed inside the entire catheter 32, a front end of the intake tube 36 is located inside a front section of the needle 31, and a rear end thereof is inserted into the head tube 371, and secured and sealed.

The connecting portion 373 is configured to be buttjointed with the pin tube 113 in the valve assembly. For example, the connecting portion 373 includes an inner threaded portion, which is connected to a threaded portion at the front end of the pin tube 113 to achieve a connection between the needle catheter assembly 3 and the valve assembly 1.

In one of the implementations, to collaborate with the above-mentioned rapid gas discharging achieved by the pressure relief groove 1113, the first exhaust vent 131, and the second exhaust vent 132, the connecting portion is provided with a pressure relief vent 374, an end of the pressure relief vent 374 is in communication to a compartment between the pin 111 and an inner wall of the pin tube 113, and another end of the pressure relief vent 374 is in direct or indirect communication to the first exhaust vent 131 in the valve assembly 1.

When the pin is not inserted into the gas cylinder, that is, when the pin is not located at the intake position, the gas discharged to the compartment between the pin 111 and the inner wall of the pin tube 113 is capable of sequentially flowing through the pressure relief vent 374, the first exhaust vent 131, and an inner cavity of the valve housing 13 to be discharged to the second exhaust vent 132, and further the gas may be discharged to a tail exhaust vent 61 of the gas bottle cover 6 through the second exhaust vent 132. The gas cylinder 5 may be disposed in the gas cylinder cover 6.

In an implementation, to implement gas return of the gas in the needle, the needle catheter assembly 3 further includes a return pipe 33 and a connector housing 38. The connector structure 37 may be disposed inside the connector housing 38. The connector housing 38 is provided with a connector exhaust vent (not shown), which may specifically be located at a fixing plate (not shown) inside the connector housing 38. The return pipe 33 is connected between the catheter 32 and the connector structure 37, disposed around an outer side of the intake tube 33, and in communication to the compartment between the catheter 32 and the intake tube 36. A pipe wall of the return pipe 33 is provided with a return vent 331.

The gas returning to the compartment between the catheter 32 and the intake tube 36 is capable of sequentially flowing through the return pipe 33, the return vent 331, an inner cavity of the connector housing 38, the connector exhaust vent, the first exhaust vent 131, and an inner cavity of the valve housing 13 to be discharged to the second exhaust vent 132, and further the gas may be discharged to a tail exhaust vent 61 of the gas bottle cover 6 through the second exhaust vent 132. The gas cylinder 5 may be disposed in the gas cylinder cover 6.

In an example, the needle catheter assembly 3 may further include a front squeezing tube 34 and a rear squeezing tube 35. The front squeezing tube 34 sleeves the catheter 32 and achieves a connection and sealing between the needle 31 and the catheter 32 by squeezing the catheter 32. The rear squeezing tube 35 sleeves the catheter 32 and achieves a connection and sealing between the return pipe 33 and the catheter 32 by squeezing the catheter 32. The rear end of the return pipe 33 sleeves the head tube 371, and is secured and sealed.

In an example, the needle catheter assembly 3 may further include a bending-proof member 39 sleeving the catheter 32 and the rear squeezing tube 35. The connector housing 38 may secure the bending-proof member 39 to the connector structure 37.

In addition, the above-mentioned needle catheter assembly 3 may be disposal, and further an effect of avoiding a cross infection may be achieved.

In one of the implementations, the gas cylinder 5 may be a miniature gas cylinder with a smaller size, which can further facilitate the reduction of occupied area and further facilitate the simplification of an operation. It can be seen that the electromagnetic valve and the miniature gas cylinder can form an integrated structure after being connected, and then, through the integrated structure of the electromagnetic valve and the miniature gas cylinder, or the integrated structure of the electromagnetic valve, the miniature gas cylinder, and the battery pack, the transluminal cryoadhesion surgeries are enabled to completely get rid of the main machine and the large gas cylinder.

In a specific implementation process, a gas in the gas cylinder may optionally be carbon dioxide or nitrous oxide.

Figure 13:
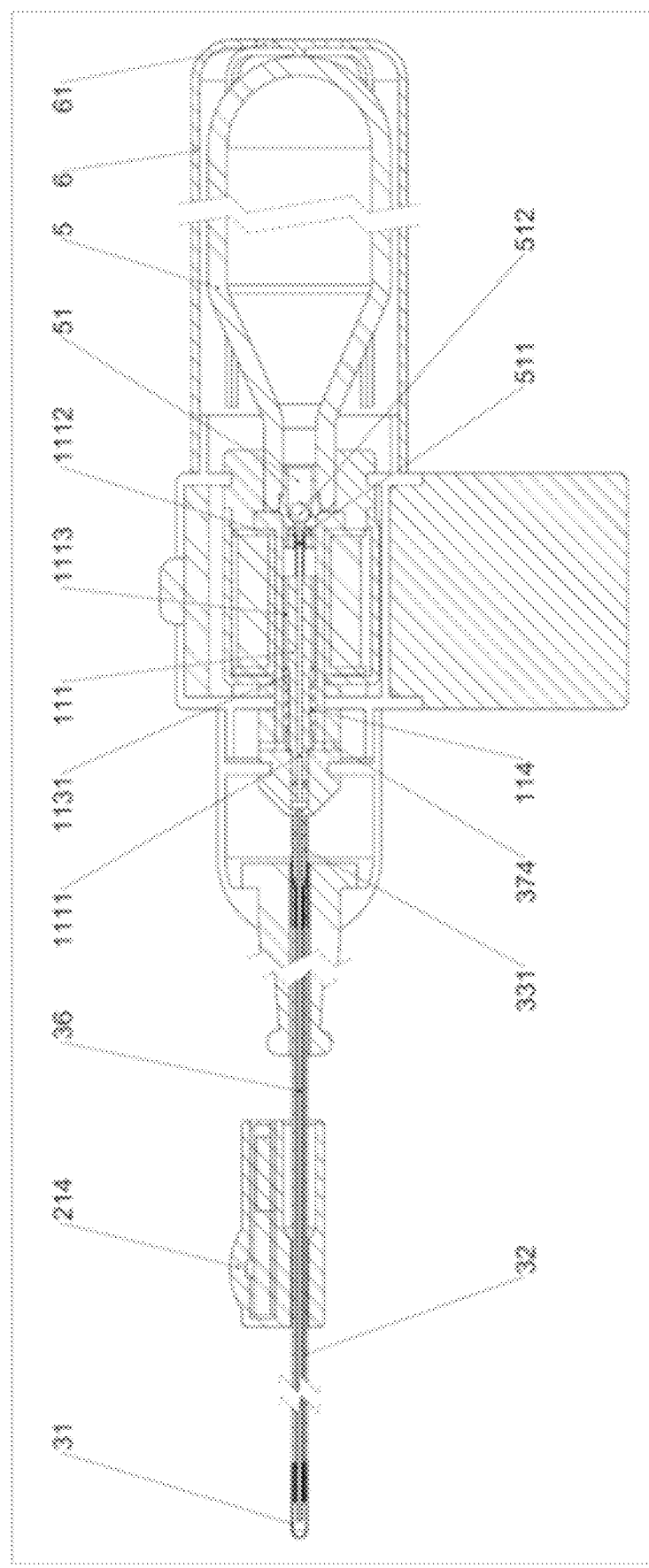
FIG. 13 is a cross-sectional view of a cryoadhesion apparatus according to an embodiment of the present invention.
Figure 14:
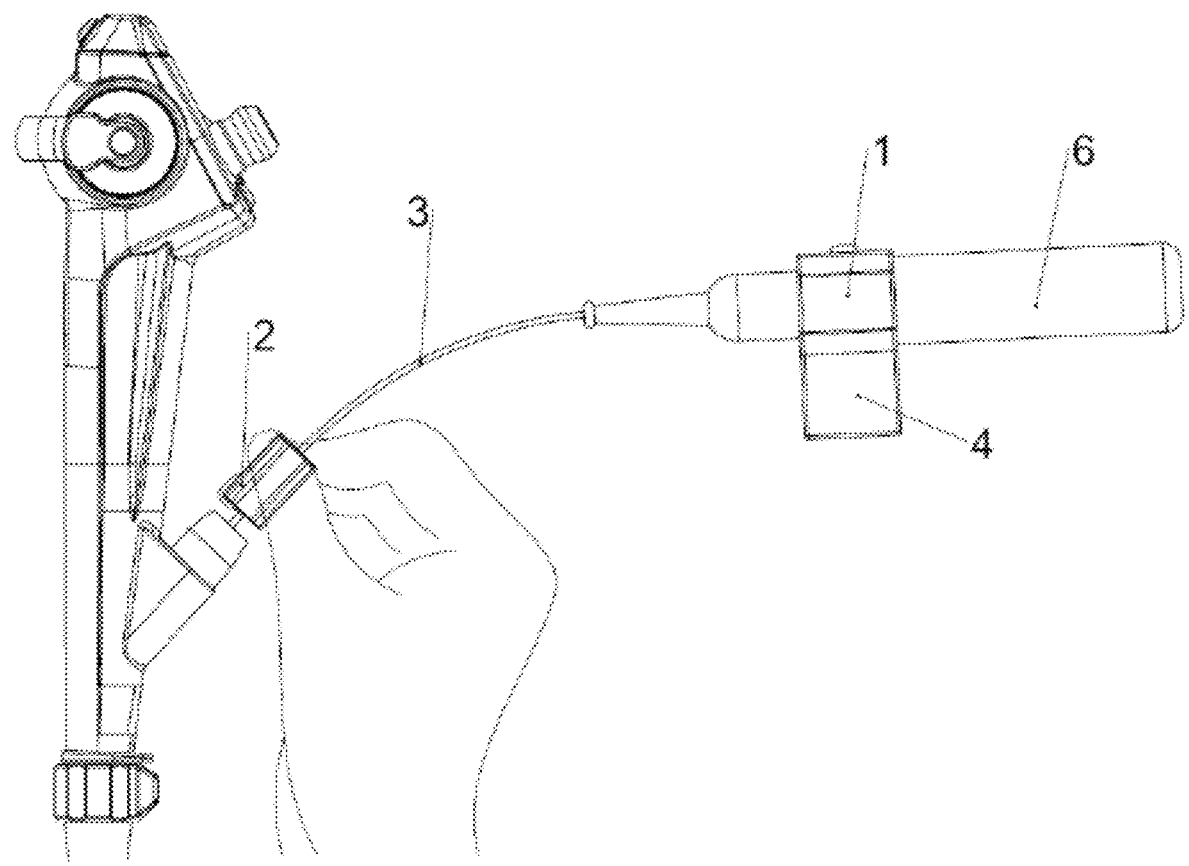
FIG. 14 is a schematic diagram of a cryoadhesion apparatus in a use state according to an embodiment of the present invention.

FIG. 13 is a cross-sectional view of a cryoadhesion apparatus according to an embodiment of the present invention. FIG. 14 is a schematic diagram of a cryoadhesion apparatus in a use state according to an embodiment of the present invention.

Referring to FIG. 13 and FIG. 14, the following describes a specific application solution. The front/forward and rear/backward (for example, front end, rear end, moving forward, or moving backward) mentioned previously and below can be understood as that: a direction close to a needle is front/forward, and the direction close to the gas bottle is rear/backward.

In the specific application solution, the remote control button 2104 is pressed and the electromagnetic valve 11 is turned on, so that the pin 111 moves backward under the action of an electromagnetic force, and a spring 114 is compressed. A rear section of the pin 111 will be inserted into the gas cylinder outlet 51, and the rear section of the pin 111 achieves an axial dynamical sealing with a front sealing mechanism 511 of the gas cylinder 5 and penetrates through a rear sealing mechanism 512. A gas in the gas bottle 5 sequentially flows through the intake vent 1112, the intake channel 1111, the intake chamber 372, and the intake tube 36 to enter the needle 31 to generate a refrigeration capacity by throttling through a Joule-Thomson effect, to implement cryoadhesion of tissues outside an outer portion of the needle. The returned gas sequentially flows through the catheter 32 (specifically referring to the compartment between the catheter 32 and the intake tube 36), the return pipe 33, the return vent 331, the connector exhaust vent, the first exhaust vent 131, the inner cavity of the valve housing 13, the rear exhaust vent 132, and the tail exhaust vent 61 to be discharged.

After cryoadhesion is completed, the remote control button 2104 is released, the electromagnetic valve 11 is turned off, and the electromagnetic force disappears. The pin 111 moves forward under the action of the pin reset part 114 such as a spring. The rear section (for example, the fourth pin section 1118) of the pin 111 leaves the gas cylinder outlet 51, and the rear sealing mechanism 512 instantly seal the gas cylinder outlet. Meanwhile, the redundant gas in the intake tube 36 and the intake channel 1111 is discharged from the intake vent 1112 to achieve the purpose of rapid gas discharging. The needle 31 is enabled to rapidly restore to a normal temperature to achieve a separation from the tissues after the adhesion. The gas discharged from the intake vent 1112 will be discharged through the pressure relief groove 1113, the pressure relief gap of the pin limit portion 1131, the compartment at which the pin reset part is located (that is, the compartment between the second pin section 1116 and the pin tube 113), the pressure relief vent 374, the first exhaust vent 131, the second exhaust vent 132, and the tail exhaust vent 61.

In actual use, some or all of the needle catheter assembly 3 and the sheath structure 21 may be disposal. The gas cylinder 5 needs to be replaced when pressure is insufficient. The battery pack 4 may be replaced with a standby battery pack when power is insufficient. The battery pack may be detached and charged separately. In an example, the remaining parts can be reused.

In addition, a sealing mechanism is provided between the left and right housings and between the housings of the parts to prevent gas returning or gas discharging from a position other than the tail exhaust vent 61.

During surgical operations, when an endoscope reaches the vicinity of a lesion, the needle 31 is inserted into the remote control assembly 2, two sides of the rear end of the remote control assembly 2 are held with a thumb and a forefinger, the squeezing channel 2101 is squeezed with the thumb and forefinger, and the catheter 32 and the remote control assembly 2 are secured by using a frictional force; the needle 31 is then pushed forward and is inserted from a forceps channel of the endoscope; the thumb and forefinger are released, and the squeezing channel 2101 is restored to the original shape; the remote control assembly is moved backward along the catheter 32; and the catheter 32 is pushed forward through squeezing by the thumb and forefinger again. This process is repeated until the needle 31 contacts the lesion. At this time, the squeezed state of the squeezing channel 2101 is maintained and the remote control button 2104 is pressed with the middle finger of the same hand to start freezing. After the needle adheres the tissue, a frozen state is continuously kept (the remote control button 2104 is pressed and held), and a lesion tissue is pulled out of a forceps channel of a tracheoscope or pulled out together with the endoscope. After the lesion tissue is pulled out, the middle finger is released to stop freezing and sampling is completed.

In conclusion, in the cryoadhesion apparatus provided in this embodiment, the needle catheter assembly passes through the catheter channel of the remote control assembly, and further, the control of freezing and the push-in/pull-out of the catheter can both be achieved based on the remote control assembly, thereby making it convenient for an operator to achieve the control of freezing and the push-in/pull-out of the catheter with one hand, and avoiding the use of a pedal, a main machine, or the like. Therefore, an operation of a transluminal cryoadhesion surgery is simplified, and the convenience and safety of the surgery are improved. In addition, in a case in which no parts such as a pedal switch are configured while an electromagnetic valve is used, space can be effectively saved.

Finally, it should be noted that the above embodiments are merely used to describe the technical solutions of the present invention, but not to limit the present invention. Although the present invention is described in detail with reference to the foregoing embodiments, a person of ordinary skill in the art shall understand that modifications may be made to the technical solutions described in the foregoing embodiments, or some or all of the technical features thereof may be equivalently substituted. However, these modifications or substitutions do not essentially depart the corresponding technical solutions from the scope of the technical solutions of the embodiments of the present invention.

What is claimed is:

1. A cryoadhesion apparatus, comprising: a remote control assembly, a valve assembly, a needle catheter assembly, and a gas cylinder, wherein the remote control assembly comprises a sheath structure and a remote control mounted in the sheath structure, the sheath structure is provided with a catheter channel for the needle catheter assembly to pass through, and two ends of the valve assembly are respectively connected to the needle catheter assembly and the gas cylinder;

the sheath structure is capable of squeezing the needle catheter assembly, wherein when squeezing is maintained, the needle catheter assembly is capable of moving along with the sheath structure under a frictional force between an inner wall of the catheter channel and the needle catheter assembly; when the sheath structure does not squeeze the needle catheter assembly, the remote control assembly is capable of moving along the needle catheter assembly;

the remote control is configured to, when triggered, send a trigger signal to the valve assembly;

the valve assembly is configured to transport, when receiving the trigger signal, a gas from the gas cylinder to the needle catheter assembly, to enable the needle catheter assembly to perform freezing;

the sheath structure comprises a remote control sleeve portion, which is provided with a trigger part and a remote control chamber configured to accommodate the remote control; and the trigger part is capable of triggering, when touched, a button switch of the remote control in the remote control chamber to enable the remote control to transmit the trigger signal when the button switch is triggered.

2. The cryoadhesion apparatus according to claim 1, wherein the sheath structure further comprises a channel base body, the catheter channel is disposed in the channel base body, and the channel base body is fixedly connected to the remote control sleeve portion.

3. The cryoadhesion apparatus according to claim 2, wherein the catheter channel in the channel base body comprises a guide channel and a squeezing channel, an inner diameter of the squeezing channel is greater than the guide channel, and an inner wall of the squeezing channel is provided with a soft and rough surface; and the inner wall of the squeezing channel is capable of deforming when a corresponding position of the channel base body is pinched and squeezing the needle catheter assembly.

4. The cryoadhesion apparatus according to claim 3, wherein an inner wall of the guide channel is provided with a rigid and smooth surface.

5. The cryoadhesion apparatus according to claim 3, wherein the valve assembly comprises an electromagnetic valve and a receiving circuit board, and the electromagnetic valve comprises a pin, a pin tube, a pin reset part, a seat, and a pin driving structure; an intake channel is provided inside the pin, the pin passes through the pin tube, an end of the pin tube is configured to be connected to the needle catheter assembly, another end of the pin tube is connected to a side of the seat, and another side of the seat is connected to the gas cylinder; an end of the pin is connected to the needle catheter assembly;

the pin driving structure is configured to, when the receiving circuit board receives the trigger signal, drive the pin to be in an intake position, at which the pin is capable of being inserted into the gas cylinder, so that the gas in the gas bottle enters the intake channel and is transported through the intake channel to the needle catheter assembly; and the pin reset part is configured to, when the pin driving structure does not drive the pin, drive the pin to reset from the intake position to a non-intake position, at which the pin is not inserted into the gas bottle.

6. The cryoadhesion apparatus according to claim 2, wherein the sheath structure further comprises a pressing plate, the catheter channel comprises a guide channel, the pressing plate is in rotary connection with the remote control sleeve portion, a side of the pressing plate and opposite to the remote control sleeve portion is provided with a squeezing groove, and an outer surface of the remote control sleeve portion is provided with a squeezing surface; the needle catheter assembly is capable of passing between the squeezing groove and the squeezing surface and passing through the guide channel, and the squeezing surface and/or an inner wall of the squeezing groove is provided with a soft and rough surface;

the pressing plate is configured to: when being pressed to rotate, squeeze the needle catheter assembly through the squeezing groove and the squeezing surface; or the pressing plate is configured such that: when the pressing plate is not pressed, the squeezing groove and the squeezing surface squeeze the needle catheter assembly, and when the pressing plate is pressed, the squeezing groove and the squeezing surface no longer squeeze the needle catheter assembly.

7. The cryoadhesion apparatus according to claim 6, wherein the sheath structure further comprises a pressing plate reset part, the pressing plate reset part is connected between the pressing plate and the remote control sleeve portion and configured to, when the pressing plate is not pressed, drive the pressing plate to rotate to reset, so that the needle catheter assembly is no longer squeezed or is squeezed.

8. The cryoadhesion apparatus according to claim 6, wherein the valve assembly comprises an electromagnetic valve and a receiving circuit board, and the electromagnetic valve comprises a pin, a pin tube, a pin reset part, a seat, and a pin driving structure; an intake channel is provided inside the pin, the pin passes through the pin tube, an end of the pin tube is configured to be connected to the needle catheter assembly, another end of the pin tube is connected to a side of the seat, and another side of the seat is connected to the gas cylinder; an end of the pin is connected to the needle catheter assembly;

the pin driving structure is configured to, when the receiving circuit board receives the trigger signal, drive the pin to be in an intake position, at which the pin is capable of being inserted into the gas cylinder, so that the gas in the gas bottle enters the intake channel and is transported through the intake channel to the needle catheter assembly; and the pin reset part is configured to, when the pin driving structure does not drive the pin, drive the pin to reset from the intake position to a non-intake position, at which the pin is not inserted into the gas bottle.

9. The cryoadhesion apparatus according to claim 2, wherein the valve assembly comprises an electromagnetic valve and a receiving circuit board, and the electromagnetic valve comprises a pin, a pin tube, a pin reset part, a seat, and a pin driving structure; an intake channel is provided inside the pin, the pin passes through the pin tube, an end of the pin tube is configured to be connected to the needle catheter assembly, another end of the pin tube is connected to a side of the seat, and another side of the seat is connected to the gas cylinder; an end of the pin is connected to the needle catheter assembly;

the pin driving structure is configured to, when the receiving circuit board receives the trigger signal, drive the pin to be in an intake position, at which the pin is capable of being inserted into the gas cylinder, so that the gas in the gas bottle enters the intake channel and is transported through the intake channel to the needle catheter assembly; and the pin reset part is configured to, when the pin driving structure does not drive the pin, drive the pin to reset from the intake position to a non-intake position, at which the pin is not inserted into the gas bottle.

10. The cryoadhesion apparatus according to claim 1, wherein at least one of the sheath structure, the remote control and the needle catheter assembly is disposable.

11. The cryoadhesion apparatus according to claim 1, wherein the valve assembly comprises an electromagnetic valve and a receiving circuit board, and the electromagnetic valve comprises a pin, a pin tube, a pin reset part, a seat, and a pin driving structure; an intake channel is provided inside the pin, the pin passes through the pin tube, an end of the pin tube is configured to be connected to the needle catheter assembly, another end of the pin tube is connected to a side of the seat, and another side of the seat is connected to the gas cylinder; an end of the pin is connected to the needle catheter assembly;

the pin driving structure is configured to, when the receiving circuit board receives the trigger signal, drive the pin to be in an intake position, at which the pin is capable of being inserted into the gas cylinder, so that the gas in the gas bottle enters the intake channel and is transported through the intake channel to the needle catheter assembly; and the pin reset part is configured to, when the pin driving structure does not drive the pin, drive the pin to reset from the intake position to a non-intake position, at which the pin is not inserted into the gas bottle.

12. The cryoadhesion apparatus according to claim 11, wherein the pin comprises a first pin section, a second pin section, a third pin section, and a fourth pin section that are sequentially connected; the first pin section is inserted into an intake chamber of the needle catheter assembly; the fourth pin section is configured to be inserted into the gas cylinder; and an outer diameter of the third pin section matches an inner diameter of the pin tube, an outer diameter of the second pin section is less than an outer diameter of the third pin section, and the pin reset part is disposed on an outer side of the second pin section.

13. The cryoadhesion apparatus according to claim 12, wherein a side wall of the fourth pin section is provided with an intake vent, and when the pin is inserted into the gas cylinder, a gas is capable of entering the intake channel from the intake vent.

14. The cryoadhesion apparatus according to claim 13, wherein an inner side of the pin tube is fixedly provided with a pin limit portion, and the pin reset part is connected to the pin limit portion; and the pin limit portion is capable of blocking an end of the third pin section that is far away from the gas bottle, and the pin reset part is located at the outer side of the second pin section to limit a motion position of the pin when reset.

15. The cryoadhesion apparatus according to claim 14, wherein the pin limit portion comprises at least two fan-shaped limit portions, which are arranged at an interval along a circumferential direction of the pin to form a pressure relief gap between two adjacent fan-shaped limit portions;

the third pin section is provided with a pressure relief groove running through two ends of the third pin section; and when the pin is not inserted into the gas cylinder, a gas in the intake channel is capable of sequentially flowing through the intake vent, the pressure relief groove, and the pressure relief gap to be discharged to a compartment between the second pin section and an inner wall of the pin tube.

16. The cryoadhesion apparatus according to claim 12, wherein the outer side of the second pin section is provided with a pin outer thread, which matches and is connected to a limit nut, and the pin reset part is connected to the limit nut; and the limit nut is capable of adjusting a position of the limit nut relative to the pin by rotating relative to the pin outer thread to change a compression amount or an expansion amount of the pin reset part.

17. The cryoadhesion apparatus according to claim 11, wherein the needle catheter assembly comprises a needle, a catheter, and a connector structure that are sequentially connected, an intake tube is provided inside the catheter, the connector structure is connected to the valve assembly and is capable of transporting a gas from the valve assembly to the intake tube through which the gas is transported to the needle, and the catheter passes through the catheter channel.

18. The cryoadhesion apparatus according to claim 17, wherein the connector structure comprises a connector body, a connecting portion, and a head tube; an intake chamber is provided inside the connector body; the connecting portion and the head tube are respectively disposed at two ends of the connector body; and the intake chamber is configured for the pin of the valve assembly to be inserted after passing through the connecting portion, the intake tube passes through the head tube to be connected to the intake chamber, and the connecting portion is configured to be butt-jointed with the pin tube in the valve assembly.

19. The cryoadhesion apparatus according to claim 18, wherein the valve assembly further comprises a valve housing, and the electromagnetic valve and the receiving circuit board are disposed inside the valve housing; the valve housing is provided with a first exhaust vent and a second exhaust vent;

the connecting portion is provided with a pressure relief vent, an end of the pressure relief vent is in communication to a compartment between the pin and an inner wall of the pin tube, and another end of the pressure relief vent is in direct or indirect communication to the first exhaust vent in the valve assembly; and when the pin is not inserted into the gas cylinder, a gas discharged to the compartment between the pin and the inner wall of the pin tube is capable of sequentially flowing through the pressure relief vent, the first exhaust vent, and an inner cavity of the valve housing to be discharged to the second exhaust vent.

20. The cryoadhesion apparatus according to claim 17, wherein the valve assembly further comprises a valve housing, and the electromagnetic valve and the receiving circuit board are disposed inside the valve housing; and the valve housing is provided with a first exhaust vent and a second exhaust vent;

the needle catheter assembly further comprises a return pipe and a connector housing, the connector structure is disposed inside the connector housing, the connector housing is provided with a connector exhaust vent, the return pipe is connected between the catheter and the connector structure, disposed around an outer side of the intake tube, and in communication to the compartment between the catheter and the intake tube, and a pipe wall of the return pipe is provided with a return vent; and a gas returning to the compartment between the catheter and the intake tube is capable of sequentially flowing through the return pipe, the return vent, an inner cavity of the connector housing, the connector exhaust vent, the first exhaust vent, and an inner cavity of the valve housing to be discharged to the second exhaust vent.

* * * * *